United States Patent [19]

Latham et al.

[11] Patent Number: 5,767,227

[45] Date of Patent: Jun. 16, 1998

[54] IODOTHYRONINE POLYMERS

[75] Inventors: Keith Roger Latham, Rockville, Md.; Vincent Ernest Latham, Lady Lake, Fla.

[73] Assignee: Lotus Biochemical Corp., Bristol, Va.

[21] Appl. No.: 347,104

[22] Filed: Nov. 22, 1994

Related U.S. Application Data

[63] Continuation of Ser. No. 854,671, Jun. 24, 1992, abandoned, which is a continuation-in-part of Ser. No. 430,990, Nov. 3, 1989, abandoned.

[51] Int. Cl.[6] .......................... A61K 38/16; A61K 31/74
[52] U.S. Cl. .......................... 530/324; 530/325; 530/326; 530/327; 530/328; 530/329; 530/330; 514/5; 514/12; 514/13; 514/14; 514/15; 514/16; 514/17; 424/78.08
[58] Field of Search .......................... 514/5, 12–17; 424/78.08; 530/324–328

[56] References Cited

U.S. PATENT DOCUMENTS

| | | | |
|---|---|---|---|
| 4,040,907 | 8/1977 | Ullman | 195/63 |
| 4,399,121 | 8/1983 | Albarella | 260/112.5 |

*Primary Examiner*—Cecilia J. Tsang
*Assistant Examiner*—David Lukton

*Attorney, Agent, or Firm*—Oblon, Spivak, McClelland, Maier & Neustadt, P.C.

[57] ABSTRACT

Iodothyronine polymers having a plurality of recurring units of formula I

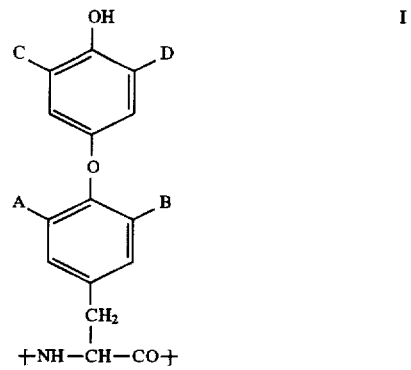

in which A is iodo and B, C and D are independently H or iodo are described. Polymers in which A and C are iodo and B and D are independently H or iodo and in which substantially all of the recurring units are L-stereoisomers, have utility in treating thyroid hormone deficiencies.

20 Claims, No Drawings

IODOTHYRONINE POLYMERS

This application is a continuation of application Ser. No. 07/854,671, filed 24 Jun. 1992, now abandoned, which is a continuation in part of application Ser. No. 07/430,990, filed Nov. 3, 1989, now abandoned.

This invention relates to iodothyronine polymers which have utility in the treatment of thyroid hormone deficiencies, to pharmaceutical compositions containing iodothyronine polymers and to the use of iodothyronine polymers in the treatment of thyroid hormone deficiencies. The iodothyronine polymers of the present invention contain recurring units linked by —NHCO— bridging groups and are therefore polypeptides.

Thyroid hormone deficiencies are disease states in which insufficient thyroid hormone is released in the body causing a slowing down of all the metabolic processes of the body and, in children, causing poor mental and physical development. Dessicated thyroid glands obtained from the ox, sheep or pig have been used for many years to treat thyroid hormone deficiencies. However the actual thyroid hormone dose from dessicated thyroid glands is difficult to regulate due to variations in iodine content between preparations. More recently synthetic levothyroxine ($LT_4$) has been used to treat thyroid hormone deficiencies.

The present invention provides a substantially pure synthetic iodothyronine polymer having a plurality of recurring units, which may be the same or different, of formula I

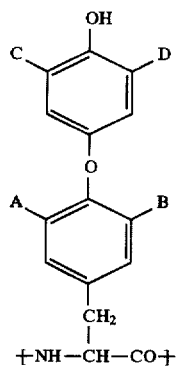

in which A is iodo and B, C and D are independently H or iodo. In preferred iodothyronine polymers substantially all of the recurring units of formula I are in the same stereoisomeric form. In particularly preferred iodothyronine polymers substantially all of the recurring units of formula I are L-stereoisomers. In preferred iodothyronine polymers A and C are iodo and B and D are independently H or iodo. In particularly preferred iodothyronine polymers A and C are iodo and at least one of B and D is iodo. The average number of the recurring units may vary from about 5 to about 400, preferably from about 10 to about 400, more preferably from about 20 to about 200, or from about 30 to about 150 or from about 80 to about 120.

The recurring units of formula I are derivatives of one or more iodothyronine compounds selected from the group consisting of $3-T_1$, $3,3'-T_2$, $3,5-T_2$, $rT_3$, $T_3$ and $T_4$ as defined in Table I below.

TABLE I

| | |
|---|---|
| 3,3',5,5'-Tetraiodothyronine | $T_4$ |
| 3,3',5-Triiodothyronine | $T_3$ |
| 3,3',5'-Triiodothyronine | $rT_3$ |

TABLE I-continued

| | |
|---|---|
| 3,5-Diiodothyronine | $3,5-T_2$ |
| 3,3'-Diiodothyronine | $3,3'-T_2$ |
| 3-Monoiodothyronine | $3-T_1$ |

When the iodothyronine polymers of the present invention are used to treat thyroid hormone deficiencies, substantially all of the recurring units of formula I are the physiologic L-stereoisomer. That is, at least 90%, preferably 95%, and most preferably greater than 99% of the recurring units are the physiologic L-stereoisomer. In the iodothyronine polymers used to treat thyroid hormone deficiencies, the recurring units of formula I are derivatives of the pharmacologically active iodothyronine compounds identified in Table II.

TABLE II

| | | |
|---|---|---|
| 3,3',5,5'-Tetraiodo-L-thyronine | Thyroxine | $LT_4$ |
| 3,3',5-Triiodo-L-thyronine | Liothyronine | $LT_3$ |
| 3,3',5'-Triiodo-L-thyronine | Reverse $T_3$ | $rLT_3$ |
| 3,3'-Diiodo-L-thyronine | — | $3,3'-LT_2$ |

In one embodiment of the invention the iodothyronine polymer is a homopolymer as defined below in Table III.

TABLE III

| | Substitution in Formula I | | | |
|---|---|---|---|---|
| Abbreviation | A | B | C | D |
| poly-$T_4$ | I | I | I | I |
| poly-$T_3$ | I | I | I | H |
| poly-$rT_3$ | I | H | I | I |
| poly-$3,5-T_2$ | I | I | H | H |
| poly-$3,3'-T_2$ | I | H | I | H |
| poly-$3-T_1$ | I | H | H | H |

In each such homopolymer, substantially all of the recurring units will be those identified above. That is, at least 90%, preferably at least 95%, and most preferably at least 99% of the recurring units of each homopolymer will contain the substituents identified in Table III. The iodothyronine homopolymers in which substantially all of the recurring units of formula I are L-stereoisomers and in which A, B, C and D are iodo, or in which A, B and C are iodo and D is H have utility in the treatment of thyroid hormone deficiency. The preferred homopolymers for use in therapy are poly-$LT_4$ and poly-$LT_3$.

The iodothyronine polymers of the present invention in which substantially all of the recurring units of formula I are L-stereoisomers and A and C are iodo and B and D are independently H or iodo have utility in the treatment of thyroid hormone deficiencies in human and other mammals. $LT_4$ is the primary thyroid hormone in mammals, but $LT_3$ is also released by the thyroid gland and is also active as a thyroid hormone. $LT_4$ and $LT_3$ are found in the blood in an approximate 4:1 ratio. In one embodiment of the present invention, the iodo-thyronine polymer contains recurring units derived from both $LT_4$ and $LT_3$ to form a copolymer of these units. Preferably, from about 70 to about 90% of the recurring units are the $LT_4$ derivatives and about 10 to about 30% of the recurring units are the $LT_3$ derivatives. Most preferably, the ratio is approximately 4:1 i.e. about 80% of the recurring units are $LT_4$ and approximately 20% of such units are $LT_3$. This copolymer is referred to herein as poly-$LT_4$/$LT_3$.

It has been found that $rLT_3$ may also have a role in thyroid hormone function in humans and other mammals. A further aspect of the present invention provides an iodothyronine polymer in which a fraction of the recurring units are derived from $rLT_3$. In such an iodothyronine polymer, approximately 70–89% of the recurring units are derived from $LT_4$, approximately 10–29% of the recurring units are derived from $LT_3$, and the remainder of the recurring units are derived from $rLT_3$. Most preferably, approximately 80% of such units are derived from $LT_4$, approximately 15% of such units are derived from $LT_3$, and approximately 5% of such units are derived from $rLT_3$. This heteropolymer is referred to herein as poly-$LT_4$/$LT_3$/$rLT_3$.

A further aspect of the present invention provides iodothyronine polymers which contain further recurring units of formula II

II in which R is a residue of any of the amino acids commonly found in nature. These amino acids are listed by Lehninger in Principles of Biochemistry (1982) published by Worth Publishers Inc of New York (see page 96) as alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine. The properties of the iodothyronine polymers are modified by copolymerization with these amino acids. For example, if greater aqueous solubility is desired, hydrophilic amino acids, like lysine, arginine, aspartic acid, glutamic acid, serine or threonine can be copolymerized into the polypeptide chain. The amount of amino acid incorporated will be dependent upon the particular iodothyronine/amino acid copolymer(s), and the properties desired. The recurring units of formula II may comprise up to 50%, preferably up to 66%, most preferably up to 80% of the recurring units in the copolymers.

Iodothyronine polymers of the present invention in which substantially all of the recurring units of formula I are the L-stereoisomers and in which the recurring units are of formula I in which A and C are iodo and B and D are independently H or iodo have utility in the treatment of thyroid hormone deficiencies. A further aspect of the present invention therefore provides a pharmaceutical composition suitable for treating thyroid hormone deficiencies which comprises a pharmaceutically acceptable diluent or carrier and a pharmacologically active ingredient consisting of a pharmaceutically effective amount of a substantially pure synthetic iodothyronine polymer having a plurality of recurring units, which may be the same or different, of the formula I in which A and C are iodo and B and D are independently H or iodo, in which polymer substantially all of the recurring units of formula I are L-stereoisomers. Preferably at least one of B or D is iodo. The average number of the recurring units may vary from about 5 to about 400, preferably from about 10 to about 400, more preferably from about 20 to about 200, or from about 30 to about 150 or from about 80 to about 120. The iodothyronine polymer in these pharmaceutical compositions may be poly-$LT_4$, poly-$LT_3$, poly-$LT_4$/$LT_3$, poly-$LT_4$/$LT_3$/$rLT_3$ or mixtures thereof. Particularly preferred compositions are those in which the iodothyronine polymer is poly-$LT_4$, poly-$LT_3$, a mixture of poly-$LT_4$ and poly-$LT_3$ in which the ratio of poly-$LT_4$ to poly-$LT_3$ lies in the range 7:3 to 9:1 preferably about 4:1 or a mixture of poly-$LT_4$ poly-$LT_3$ and poly-rLT3 in which the ratio of poly-$LT_4$ to poly-$LT_3$ and poly-$rLT_3$ is approximately 80:15:5.

In therapeutic use, the iodothyronine polymer is preferably administered orally. Thus the therapeutic compositions of the present invention may take the form of any of the known pharmaceutical compositions for oral administration. Pharmaceutically acceptable carriers are well known in the art of pharmacy. The compositions of the invention may contain 0.1–90% by weight of iodothyronine polymer. The compositions of the invention are generally prepared in unit dosage form.

Compositions for oral administration are the known pharmaceutical forms for such administration, for example tablets, capsules, syrups and aqueous or oily suspensions. The diluent or carrier used in the preparation of these compositions can be any of the materials known in the pharmacists' art. Tablets may be prepared by mixing the iodothyronine polymer with an inert diluent such as calcium phosphate in the presence of disintegrating agents, for example maize starch, and lubricating agents, for example magnesium stearate, and tableting the mixture by known methods. The tablets may be formulated in a manner known to those skilled in the art so as to give a sustained release of the compounds of the present invention. Such tablets may, if desired, be provided with enteric coatings by known methods, for example by the use of cellulose acetate phthalate. Similarly, capsules, for example hard or soft gelatin capsules, containing the active compound with or without added excipients, may be prepared by conventional means and, if desired, provided with enteric coatings in a known manner. The tablets and capsules may conveniently each contain 12.5 to 500 microgrammes of the iodothyronine polymer. Other compositions for oral administration include, for example, aqueous suspensions containing the iodothyronine polymer in an aqueous medium in the presence of a non-toxic suspending agent such as sodium carboxymethylcellulose, and oily suspensions containing a compound of the present invention in a suitable vegetable oil, for example arachis oil.

An alternative route of administration of the iodothyronine polymer is by means of an implant. In this case a pellet containing iodothyronine polymers containing large numbers of recurring units is implanted under the skin of the patient and pharmacologically active amounts of the iodothyronine polymer are then released over an extended period of time, suitably over several weeks or months.

In some formulations it may be beneficial to use the compounds of the present invention in the form of particles of very small size, for example as obtained by fluid energy milling.

The pharmaceutical compositions containing a therapeutically effective amount of the iodothyronine polymers of the present invention in which substantially all of the recurring units of formula I are the L-stereoisomers may be used to treat thyroid hormone deficiencies in warm blooded animals including human beings. In such treatment the amount of the iodothyronine polymer administered per day is under the control of the prescribing physician and will depend inter alia on the age of the patient and on the severity of the condition to be treated but will usually lie in the range 12.5 to 1000 micrograms per day, preferably 25 to 400 micrograms per day, most preferably 50 to 300 micrograms per day given in single or divided doses at one or more times during the day. In the case of iodothyronine polymers containing recurring units of formula II, the amount of the polymer administered may be higher than quoted above but will be such as to give rise to equivalent amounts of the pharmacologically active iodothyronine moieties.

A preferred method of synthesizing the iodothyronine polymers of the present invention comprises the polymerisation of one or more N-carboxyanhydrides (NCA) of formula III

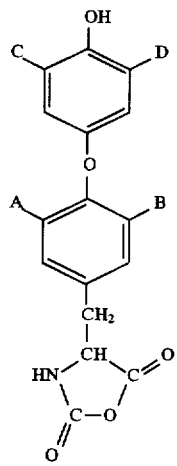

in which A is iodo, and B, C, and D are H or iodo. Suitable N-carboxyanhyrides of formula III are identified in Table IV.

TABLE IV

| Abbreviation | Substitution in Formula III | | | |
|---|---|---|---|---|
| | A | B | C | D |
| $T_4$-NCA | I | I | I | I |
| $T_3$-NCA | I | I | I | H |
| $rT_3$-NCA | I | H | I | I |
| 3,5-$T_2$-NCA | I | I | H | H |
| 3,3'-$T_2$-NCA | I | H | I | H |
| 3-$T_1$-NCA | I | H | H | H |

When the desired iodothyronine polymer is one in which substantially all of the recurring units are in the same stereoisomeric form (preferably the L-stereoisomeric form), the N-carboxyanhydride of formula III should be substantially all in that same stereoisomeric form.

When the desired iodothyronine polymer is a homopolymer, one N-carboxyanhydride of formula III is used. However, if the desired iodothyronine polymer is a copolymer or heteropolymer, then two or more N-carboxyanhydrides of formula III are used in the same molar proportions as is desired in the iodothyronine polymer. For example, when the desired iodothyronine polymer is a copolymer of $LT_4$ and $LT_3$, the N-carboxy-anhydrides of $LT_4$ and of $LT_3$ are used in the molar ratio desired in the iodothyronine copolymer and when the desired iodothyronine polymer is a heteropolymer of $LT_4$, $LT_3$ and $rLT_3$, the N-carboxyanhydrides of $LT_4$, $LT_3$ and $rLT_3$ are used in the molar ratio desired in the final copolymer. When the iodothyronine polymer also contains one or more further recurring units of formula II, an N-carboxyanhydride of formula IV

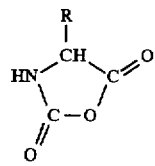

may be used in addition to the N-carboxyanhydride of formula III. The N-carboxyanhydrides of formula III and formula IV are used in the molar ratio desired in the final iodothyronine polymer.

The polymerization preferably comprises reacting one or more compounds of formula III in an anhydrous solvent, preferably at a concentration of about 5-40% and a temperature from about 0° C. to the boiling point of the solvent for sufficient time to complete the polymerisation. The reaction is continued until polymerisation is complete as indicated, for example, by product precipitation, cessation of $CO_2$ evolution, the attainment of maximum viscosity or the absence of the starting material, as indicated for example, by spectroscopic examination of the reaction mixture. Examples of suitable anhydrous solvents include ethers, such as dioxane or tetrahydrofuran, aromatic solvents, such as benzene, chlorobenzene, and toluene, and other solvents, such as dimethyl formamide, ethyl acetate and dimethyl sulphoxide. A preferred solvent is dioxane or tetrahydrofuran.

Preferably, a base is used as an initiator in the above reaction. An inorganic or organic base may be used, although an organic base is preferred. Examples of suitable bases include organic amines such as n-butylamine, triethylamine, tributylamine, triamylamine, diisopropylethylamine or alkali metal alkoxides such as sodium methoxide or sodium ethoxide. The molar ratio of the N-carboxyanhydride derivative of formula III to the initiator lies in the range 20 to 400 preferably 30 to 150 more preferably 50 to 100. Most preferably, the base is sodium methoxide.

The iodothyronine polymers of the present invention may be prepared by the further iodination of iodothyronine polymers having recurring units of formula I in which A is iodo, B is H or iodo and C and D are H. These iodothyronine polymer starting materials are identified in Table III as poly-3,5-$T_2$ and poly-3-$T_1$ respectively. If these polymers are subjected to vigorous iodination conditions, for example by the use of excess potassium triiodide or of iodine monochloride as the iodinating agent, iodothyronine polymers can be produced in which both C and D are iodo. Thus poly-3,5-$LT_2$ gives poly-$LT_4$ and poly-3-$LT_1$ , gives poly-$rLT_3$. By using less vigorous iodination conditions, for example potassium triiodide in diethylamine, it is possible to produce iodothyronine polymer in which C is iodo and D is H. Thus poly-3,5-$LT_2$ would give poly-$LT_3$ and poly-3-$LT_1$ would give poly-3,3'-$LT_2$. By choosing iodination conditions in which iodination is incomplete, for example by restricting the amount of iodinating agent, it is possible to produce iodothyronine polymers in which C is iodo and in which D is iodo in only some of the recurring units. For example, copolymers of $LT_4$ and $LT_3$ may be prepared by partial iodination of poly-3,5-$LT_2$.

The iodothyronine polymers of the present invention may also be prepared by the condensation of the amino acids from which the recurring units of formula I are derived in the presence of a dehydrating agent such as dicyclohexylcarbodiimide which is converted into dicyclohexylurea when it removes the elements of water from two amino acid residues to form a peptide bond between them. Copolymers and hetero-polymers may be prepared by condensing mixtures of two or more amino acids.

Homogeneous polymerizations to form hetero-polymers result in a random distribution of each component in the polymer. However, when sequence-specific copolymer or heteropolymer combinations are desired, a solid phase synthesis of the Merrifield type is useful. The preferred method of synthesis is through the t-BOC or f-MOC intermediates of the iodothyronines and other amino acids if applicable. Synthesis proceeds as previously described in Groginski, Amer. Biotech. Lab., May/June:38–51 (1986), incorporated herein by reference.

The N-carboxyanhydride of formula III may be prepared by reacting the appropriate iodothyronine with a carbonylating reagent to form the N-carboxyanhydride. More particularly, they are synthesized by reacting a compound represented by the formula V

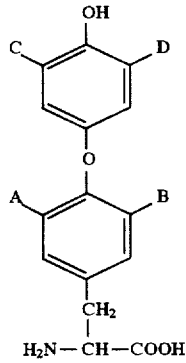

or a salt thereof with a carbonylating reagent and recovering the reaction product. Preferably, the reaction takes place in the presence of an anhydrous solvent, such as tetrahydrofuran (THF), but other appropriate solvents known to those skilled in the art can be used. A preferred carbonylating reagent is hexachlorodimethylcarbonate, $(CCl_3O)_2CO$. This normally solid chemical is commercially available from Aldrich Chemicals under the trade name Triphosgene. Typically, the iodothyronine is suspended in the anhydrous solvent and the hexachlorodimethylcarbonate is added. An excess of the hexachlorodimethylcarbonate is used. Alternatively, phosgene gas may be used as the carbonylating agent.

After it has been prepared the iodothyronine polymer may be precipitated and the resulting solid collected by filtration and may be further purified, if necessary, by recrystallisation. The product is advantageously dried by lyophilisation. In this process the precipitated iodothyronine polymer, if necessary following recrystallisation, is prefrozen or frozen in situ by evaporative cooling in vacuo with sufficient external heat provided to obtain a product with the desired, preferably less than 0.1%, moisture content.

The N-carboxyanhydrides of formula III obtained by the above synthesis are typically recrystallised to obtain intermediates of pharmaceutical purity. Since the prepared anhydrides are moisture sensitive, special care to ensure anhydrous conditions of the reaction, recovery and storage of the N-carboxyanhydrides is important. This synthetic procedure may also be used to prepare the N-carboxyanhydride derivatives of formula IV for copolymerization or heteropolymerisation with the N-carboxyanhydride derivatives of formula III to prepare iodothyronine polymers having further recurring units of formula II.

Compounds of formula V are prepared by methods which are well known in the art such as those described, for example, in U.S. Pat. Nos. 2,579,668, 2,886,592, 2,889,363, 2,889,364, 3,477,954 and 3,577,535.

The iodothyronine polymers of the present invention provide a method of delivering thyroid hormones to a patient in need thereof. Because the thyroid hormones are released by digestive proteolysis of the iodothyronine polymers of this invention, it is expected that the use of the iodothyronine polymers would have a long physiologic effect because of the sustained release from the polymers of the monomeric thyroid hormones. The use of copolymers containing recurring units derived from two or more thyroid hormones or mixtures of homopolymers of the thyroid hormones in the appropriate ratio provides a means whereby the naturally occurring ratio of thyroid hormones may be duplicated. Attempts have been made before to duplicate this naturally occurring ratio by administering a mixture of $LT_3$ and $LT_4$ (see for example U.S. Pat. Nos. 3,477,954 and 3,577,535). However, $LT_3$ has a short half life in the blood compared to the half life of $LT_4$ and so the desired ratio cannot be maintained over a long period of time. The iodothyronine polymers of the present invention are solid materials which may be readily handled and formulated to give stable, consistent pharmaceutical compositions for the treatment of thyroid hormone deficiencies.

The invention will now be illustrated by the following Examples.

EXAMPLE 1

Hexachlorodimethylcarbonate (10 g) was added to a suspension of 3,5-diodo-L-thyronine (26.3) in anhydrous tetrahydrofuran (125 ml) and the mixture was heated to 67° C. for 15 minutes. Anhydrous tetrahydrofuran (500 ml) and then anhydrous hexane (3000 ml) were added and the mixture stored at 20° C. for three hours. 3,5-Diodo-L-thyronine N-carboxyanhydride (3,5-$LT_2$-NCA) was collected by filtration. Yield 24 g.

EXAMPLE 2

A solution of 3,5-diiodo-L-thyronine N-carboxyanhydride (1 g) in dioxane (10 ml) was stirred rapidly and a 1% solution of sodium methoxide in methanol (0.05 ml) was added. The mixture was stirred for six days at ambient temperature and then petroleum ether (20 ml) was added and the resulting slurry triturated with petroleum ether. Polymeric 3,5-diodo-L-thyronine (poly 3,5-$LT_2$) was collected by filtration and dried in vacuo. Yield 0.96 g.

EXAMPLE 3

In a similar manner to that described in Example 1, 3,3', 5-triiodo-L-thyronine N-carboxyanhydride ($LT_3$-NCA) was prepared in 65% yield and polymerised to give polymeric 3,3 ', 5-triodo-L-thyronine (poly-$LT_3$) in 62% yield in a similar manner to that described in Example 2.

EXAMPLE 4

In a similar manner to that described in Example 1, 3,3',5,5'-tetraiodo-L-thyronine ($LT_4$-NCA) was prepared in 22% yield from 3,3', 5,5'-tetraiodo-L-thyronine which had been dried in vacuo at 100° C. for 17 hours and then polymerised to give polymeric 3,3',5,5'-tetraiodo-L-thyronine (poly-$LT_4$) in 82% yield in a similar manner to that described in Example 2.

EXAMPLE 5

In a similar manner to that described in Example 1, 3,5,5'-triiodo-L-thyronine N-carboxyanhydride (r$LT_3$-NCA) was prepared in 51% yield and polymerised to give polymeric 3,5,5'-triodo-L-thyronine (poly-r$LT_3$) in 70% yield in a similar manner to that described in Example 2.

EXAMPLE 6

A mixture of 4 parts of 3,3', 5,5'-tetraiodo-L-thyronine N-carboxyanhydride ($LT_4$-NCA) prepared in a similar manner to that described in Example 1 and 1 part of 3,3', 5-triiodo-L-thyronine N-carboxyanhydride ($LT_3$-NCA) prepared in a similar manner to that described in Example 3 was polymerised in a similar manner to that described in Example 2 to give a polymer containing recurring units derived from both $LT_3$ and $LT_4$ (poly $LT_4/LT_3$) in 62% yield.

EXAMPLE 7

A mixture of 80 parts 3,3', 5,5'-tetraiodo-L-thyronine N-carboxyanhydride ($LT_4$-NCA) prepared in a similar manner to that described in Example 4, 15 parts of 3,3', 5-triiodo-L-thyronine N-carboxyanhydride ($LT_3$-NCA) prepared in a similar manner to that described in Example 3 and 5 parts of 3,5,5'-triiodo-L-thyronine N-carboxyanhydride ($rLT_3$-NCA) prepared in a similar manner to that described in Example 5 was polymerised in a similar manner to that described in Example 2 to give a heteropolymer containing recurring units derived from $LT_4$, $LT_3$ and $rLT_3$ (poly $LT_4/LT_3/rLT_3$). The product was precipitated from the reaction mixture by addition of petroleum ether (2 volumes) and the precipitate dried in vacuo. Yield 55%.

EXAMPLE 8

Polymeric 3,5-diiodo-L-thyronine (poly-3,5-$LT_2$-22 g prepared in a similar manner to that described in Example 2) was dissolved in a 33% aqueous solution of diethylamine at 16° to 22° C. A 1.9N iodine solution in concentrated aqueous potassium iodide solution (88 ml) was added with stirring. The mixture was stirred at 4° to 10° C. for 2 hours. A precipitate formed which was collected by filtration and washed with water. The filter cake was dissolved in a mixture of ethanol (25 ml) and 2N aqueous sodium hydroxide solution (100 ml). 2N Hydrochloric acid was added to neutralise the solution and a precipitate formed which was collected by filtration and washed with water. The wet filter cake was placed in a freeze drying chamber in vacuo (less than 0.3 mm Hg) to freeze the cake via evaporative cooling. Sufficient heat was provided (shelf temperature 40° C.) to reduce the moisture content to less than 0.1% in 24 hours. The product was polymeric 3,3', 5,5'-tetraiodo-L-thyronine. Yield 27 g.

EXAMPLE 9

Polymeric 3,5-diiodo-L-thyronine (poly-3,5-$LT_2$-18.4 g prepared in a similar manner to that described in Example 2) was dissolved in 33% aqueous diethylamine (185 ml). A solution of potassium triiodide [82 ml of a solution prepared from iodine (26.2 g), potassium iodide (67.8 g) and water (90 ml)] was added with stirring over 30 minutes. Stirring was continued for 15 minutes and water (111 ml) and then 2N hydrochloric acid were added to cause precipitation. The brown precipitate was collected by filtration and the filter cake dissolved in a mixture of ethanol (1332 ml) and 1N aqueous sodium hydroxide solutions (111 ml). The solution was filtered, heated to boiling and treated with 30% aqueous acetic acid until precipitation commenced. The mixture was cooled in ice and the precipitate collected by filtration and washed with water. The wet filter cake was placed in a freeze drying chamber in vacuo (less than 0.3 mm Hg) to freeze the cake via evaporative cooling. Sufficient heat was provided (shelf temperature 40° C.) to reduce the moisture content to less than 0.1% in 24 hours. (Yield 24.6 g).

The product was hydrolysed with acid and high performance liquid chromatography (HPLC) of the hydrolysed product showed the presence of 83.3% $LT_4$, 16.4% $LT_3$ and less than 0.1% of 3,5-$LT_2$ indicating that the product was a polymer containing recurring units derived from $LT_4$ and $LT_3$ (poly $LT_4/LT_3$).

EXAMPLE 10

In a similar manner to that described in Example 8, polymeric 3-iodo-L-thyronine (poly-3$LT_1$) was diiodinated to give polymeric 3,5,5'-triiodo-L-thyro-nine (poly-$rLT_3$) in 96% yield. Polymeric 3-iodo-L-thyronine was prepared in a similar manner to that described in Example 2 by polymerisation of 3-iodo-L-thyronine N-carboxyanhydride (3-$LT_1$-NCA) which was prepared in 93% yield in a similar manner to that described in Example 1.

EXAMPLE 11

Direct co-polymerization of $LT_4$ and glycine was effected by suspending 3,3', 5,5'-tetraiodo-L-thyronine (3.88 g) and glycine (Zwitterionic forms) (0.37 g) in anhydrous dioxane (50 ml). Dicyclohexylcarbodiimide (2.47 g) was added with stirring and the reaction was stirred for 4 days at 17° –22° C. Acetic acid (0.2 ml) was added to decompose excess dicyclohexylcarbodiimide and petroleum ether (50 ml) was added to precipitate the polymeric product. The product was collected by filtration and the filter cake triturated with ethanol. The polymeric product was dried in vacuo. Yield 5.22 g. HPLC analysis of the acid hydrolysis of the product showed a 50/50 mixture of $LT_4$ and glycine.

EXAMPLE 12

Boc-protected $LT_4$ and glycine are prepared as described in Tam et al., *Int. J. Peptide Protein Res.*, 21:57 (1983), and polymerized by standard sequential additions on polystyrene beads as an immobilized support. The following coupling sequence is used as described in Spatola, *Amer. Biotech Lab.*, Dec. 14–22 (1984).

| Stage | Reagent | Repeat | Time |
| --- | --- | --- | --- |
| 1 | Methylene chloride | 5 | 1 |
| 2 | TFA | 1 | 5 |
| 3 | TFA | 1 | 25 |
| 4 | Methylene chloride | 4 | 1 |
| 5 | Diisopropylethylamine | 2 | 2 |
| 6 | Methylene chloride | 3 | 1 |
| 7 | DMF | 3 | 1 |
| 8 | Boc-glycine | — | 1 |
| 9 | DCC | — | — |
| 10 | DMF | 1 | 1 |
| 11 | Methylene chloride | 3 | 1 |
| 12 | Ethanol | 3 | 1 |
| 13 | DMF | 3 | 1 |
| 14 | Boc—$LT_4$ | — | 1 |
| 15 | DCC | — | — |
| 16 | DMF | 3 | 1 |
| 17 | Methylene chloride | 3 | 1 |
| 18 | Ethanol | 3 | 1 |

Steps 7 through 18 are repeated 25 or more times to obtain a polymer of 50 or more residues in length. Finally, the copolymer is isolated by cleavage from the resin using HF. The copolymer formed by this reaction has alternating recurring units derived from $LT_4$ and glycine.

EXAMPLE 13

Hexachlorodimethylcarbonate (20 g) was added to a suspension of the sodium salt of 3,5-diodo-L-thyronine (52.6 g) which had been dried at 100° C. in vacuo for 24 hours in anhydrous tetrahydrofuran (250 ml) and the mixture was heated to 65° C. The reaction mixture was allowed to react for five minutes and the solvent was then removed by evaporation. Anhydrous ethyl acetate (50 ml) and then anhydrous dichloromethane (140 ml) were added and the mixture cooled at 4° C. for one hour. 3,5-Diodo-L-thyronine N-carboxyanhydride (3,5-$LT_2$-NCA) was collected by filtration, washed with anhydrous hexane and dried in vacuo without heating. Yield 37.6 g.

EXAMPLE 14

A solution of 3,5-diiodo-L-thyronine N-carboxyanhydride (37.2 g) in ethyl acetate (372 ml which had been dried over potassium carbonate) was stirred rapidly and a 1% solution of sodium methoxide in methanol (1.86 ml) was added. The mixture was stirred for four days at ambient temperature temperature and then polymeric 3,5-diodo-L-thyronine (poly 3,5-LT$_2$) was collected by filtration, washed with ethyl acetate and then hexane and dried in vacuo. Yield 24.9 g.

EXAMPLE 15

Polymeric 3,5-diodo-L-thyronine (0.715 g) was ground to a fine powder and dissolved with gentle warming in a mixture of dimethylformamide (8.6 ml), water (5.7 ml) and diethylamine (4.3 ml) and the solution was cooled to 5°–10° C. A solution of potassium triodide was prepared from iodine (31.5 g) and a 40% solution of potassium iodide in water (100 ml of solution). Four portions of the resulting solution (0.8 ml each) were added over 30 minutes. The reaction mixture was stirred overnight as the temperature rose to ambient and then poured into acetone (200 ml). A solid was collected by filtration and washed with degassed water. The washed solid was frozen on dry ice and lyophilised under vacuum (less than 0.3 mm Hg) using a shelf temperature of 35° C. to give polymeric 3,3',5-triodo-L-thyronine (poly-LT$_3$). Yield 0.9 g.

EXAMPLE 16

Polymeric 3,5-diido-L-thyronine (1 g) was ground to a fine powder and dissolved with gentle warming in dimethylformamide (5 ml). A mixture of glacial acetic acid (2 ml) and iodine monochloride (0.8 g) was added over twenty minutes with rapid mixing and the resulting mixture heated to 60° C. Glacial acetic acid (5 ml) and then water (12 ml) were added dropwise and the mixture was reheated to 60° C. Potassium bisulphite (0.3 g) was added and the mixture cooled in ice. The resulting precipitate was collected by filtration and washed with water. The washed solid was frozen on dry ice and lyophilised under vacuum (less than 0.3 mm Hg) using a shelf temperature of 35° C. to give polymeric 3,3', 5,5'-tetraiodo-L-thyronine (poly-LT$_4$). Yield 1.56 g.

EXAMPLE 17

Hexachlorodimethylcarbonate (2 g) was added to a suspension of the sodium salt of 3,3', 5-triiodo-L-thyronine (6.73 g) which had been dried at 100° C. in vacuo for 24 hours in anhydrous tetrahydrofuran (25 ml) and the mixture was heated to 65° C. The reaction mixture was allowed to react for ten minutes and the solvent was then removed by evaporation. Anhydrous ethyl acetate (7 ml) was added to dissolve the residue and then anhydrous dichloromethane (20 ml) was added and the mixture cooled at 4° C. for one hour. 3,3', 5-Triiodo-L-thyronine N-carboxyanhydride (LT$_3$-NCA) was collected by filtration, washed with anhydrous hexane and dried in vacuo without heating. Yield 2.8 g.

EXAMPLE 18

A solution of 3,3', 5-triiodo-L-thyronine N-carboxyanhydride (1.0 g) in anhydrous dioxane (10 ml) was stirred rapidly and a 1% solution of sodium methoxide in methanol (0.05 ml) was added. The mixture was stirred for four days at ambient temperature and then water (10 ml) was added with vigorous stirring. Polymeric 3,3', 5-triiodo-L- thyronine (poly-LT$_3$) was collected by filtration and washed with water. The washed solid was frozen on dry ice and lyophilised under vacuum (less than 0.3 mm Hg) using a shelf temperature of 35° C. Yield 0.68 g.

EXAMPLE 19

A suspension of the sodium salt of 3,3', 5,5'-tetraiodo-L-thyronine (1.55 g) which had been dried at 100° C. in vacuo for 24 hours in anhydrous tetra-hydrofuran was cooled and hexachlorodimethylcarbonate (0.4 g) was added. The mixture was heated to 50° C. for five minutes and the solvent removed by evaporation. The residue was treated with anhydrous ethyl acetate (10 ml) and then with anhydrous dichloromethane and was then cooled in ice. 3,3', 5,5'-Tetraiodo-L-thyronine N-carboxyanhydride (LT$_4$-NCA) was collected by filtration, washed with anhydrous hexane and dried in vacuo without heating. Yield 0.7 g.

EXAMPLE 20

A solution of 3,3', 5,5'-tetraiodo-L-thyronine N-carboxyanhydride (1.0 g) in anhydrous dioxane (10 ml) was stirred rapidly and a 1% solution of sodium methoxide in methanol (0.05 ml) was added. The mixture was stirred for four days at ambient temperature and then water (10 ml) was added with vigorous stirring. Polymeric 3,3', 5,5'-tetraiodo-L- thyronine (poly-LT$_4$) was collected by filtration and washed with water. The washed solid was frozen on dry ice and lyophilised under vacuum (less than 0.3 mm Hg) using a shelf temperature of 35° C. Yield 0.21 g.

EXAMPLE 21

The following preparation is suitable for oral administration for the treatment of thyroid hormone deficiency:

| | Component | Amount |
|---|---|---|
| 1 | Iodothyronine polymer | 10 to 300 µg (dose dependent) |
| 2 | Corn Starch | 30 mg |
| 3 | Lactose | 61 mg |
| 4 | Polyvinylpyrrolidone (PVP) | 4 mg |
| 5 | Talcum | 5 mg |
| 6 | Sodium ascorbate | 5 mg (antioxidant) |

The finely powdered iodothyronine polymer is blended to uniformity with corn starch, lactose, PVP and ascorbate, mixed into an aqueous paste with 1.0 ml H$_2$O and freeze dried (30° shelf temperature, 0.03 mm Hg). The resulting powder is mixed uniformly with talcum and pressed into tablets.

EXAMPLE 22

Hypothyroid male rats which were 2 months old and had an average weight of 95 g were prepared by surgical removal of the thyroid gland. Six to eight weeks were allowed for clearance of endogenous thyroid hormones and rats were bled from the tail vein and serum levels of LT$_3$ and LT$_4$ were measured by radioimmunoassay (RIA). Rats having high levels of LT$_4$ due to inadequate thyroidectomy were removed from the study. A control, untreated group of four thyroidectomized rats was used to test for thyroid remnant regeneration during the course of the experiment. The treatment group of six rats received 10 µg/day of the iodothyronine polymer (poly-T$_4$/T$_3$) prepared in Example 9 slurried in corn syrup orally by gavage. After 8 days of treatment, serum levels of LT$_3$ and LT$_4$ were again measured by RIA. The results obtained are shown below in which the amounts of LT$_4$ and LT$_3$ are shown in nanograms per deciliter of blood and the values quoted are the mean values for the groups of animals.

| | Before Treatment | | After Treatment | |
|---|---|---|---|---|
| | $LT_3$ (ng/dl) | $LT_4$ (µg/dl) | $LT_3$ (ng/dl) | $LT_4$ (µg/dl) |
| Control | 22 | 0.80 | 34 | 0.88 |
| Treatment | 26 | <0.28 | 284 | 16.7 |

Since the establishment of adequate blood levels of thyroid hormones is a necessary and sufficient prerequisite for the euthyroid condition, we concluded that these data demonstrate that the oral administration of the copolymer of $LT_4$ and $LT_3$ can treat thyroid hormone deficiencies resulting from insufficient thyroidal release of thyroid hormones.

EXAMPLE 23

The sodium salt of 3,3', 5,5'-tetraiodo-L-thyronine was suspended in water and dilute (1N) hydrochloric acid was added to give a pH of between 4 and 5. The mixture was shaken for 5 minutes and the solid formed was collected by filtration, washed with water and dried under vacuo at a temperature in the range 30°–50° C. The solid was 3,3', 5,5'-tetraiodo-L-thyronine.

3,3', 5,5'-Tetraiodo-L-thyronine (46.1 g) was suspended in tetrahydrofuran (400 ml) in a metal foil-wrapped vessel. The mixture was heated at 50°–55° C. under slightly reduced pressure and solvent (100 ml) was removed by distilltion. A further portion of tetrahydrofuran (100 ml) was added and the distillation repeated to collect a total of 200 ml of solvent. A solution of hexachlorodimethylcarbonate (12 g) in tetrahydrofuran (35 ml) was added at 55° C. over a period of twenty minutes and the mixture heated at 55° C. for 2 hours. A further portion of hexachlorodimethylcarbonate (6 g) in tetrahydrofuran (15 ml) was added over ten minutes and the mixture heated at 55° C. for 1.5 hours. The mixture was added to dry hexane (3.8l) at ambient temperature over 20 minutes. A yellow solid was collected by filtration, washed with hexane and dried in vacuo at 42° C. Yield 42.7 g.

A sample (35 g) of the dried product was dissolved in a mixture of ethyl acetate (240 ml) and tetrahydrofuran (90 ml) with warming. The mixture was filtered through charcoal and the tetrahydrofuran removed by distillation under reduced pressure. Additional ethyl acetate (100 ml) was added and 100 ml of solvent was removed by distillation under reduced pressure. This addition/distillation cycle was repeated twice. The volume was then reduced to 50 ml by evaporation and the solution stored at 2° C. for two hours. The resulting solid was collected by filtration, washed with ethyl acetate and dried in vacuo at 40° C. The dried solid was dissolved in a mixture of ethyl acetate (170 ml) and tetrahydrofuran (90 ml). The solvent was removed by evaporation. The residue was dissolved in ethyl acetate (100 ml) and the solvent removed by evaporation. This dissolution/evaporation cycle was repeated and the residue dissolved in ethyl acetate (100 ml). The volume was reduced to 50 ml by evaporation and the solution stored at 2° C. for two hours. The resulting solid was collected by filtration, washed with ethyl acetate and dried in vacuo at 40° C. to give 3,3', 5,5'-tetraiodo-L-thyronine N-carboxyanhydride. Yield 21.2 g.

A solution of 3,3', 5,5'-tetraiodo-L-thyronine N-carboxyanhydride (1 g) in dioxane (8 ml) was stirred at 50° C. in a metal-foil wrapped vessel. A portion (50 microliters) of a solution of sodium methoxide (67.2 mg) in methanol (10 ml) was added and the mixture stirred at 50° C. for 3.5 hours and then a further portion (50 microliters) of the above sodium methoxide solution was added and the mixture stirred at 50° C. for a total of 23 hours. A solid was collected by filtration, washed with dioxane and dried in vacuo at 50° C. to give a dioxane-insoluble fraction of polymeric 3,3', 5,5'-tetraiodo-L-thyronine. Yield 0.317 g. The filtrate was slowly added to hexane (25 ml) and the resulting solid collected by filtration, washed with hexane and dried in vacuo at 50° C. to give a dioxane-soluble fraction of polymeric 3,3', 5,5'-tetraiodo-L-thyronine. Yield 0.403 g.

EXAMPLES 24 to 27

Four solutions of 3,3', 5,5'-tetraiodo-L-thyronine N-carboxyanhydride (1 g prepared in Example 23) in dioxane (10 ml) were prepared with warming. Four solutions of sodium methoxide in methanol were made up as follows:

| Ex | Wt of NaOMe (mg) | Volume of methanol (ml) |
|---|---|---|
| 24 | 67.2 | 10 |
| 25 | 134 | 10 |
| 26 | 335 | 10 |
| 27 | 670 | 10 |

A sample (50 microliters) of one of these sodium methoxide solutions was added to each of the solutions of 3,3', 5,5'-tetraiodo-L-thyronine N-carboxyanhydride and the resulting mixtures were stored at 48°–50° C. for 23 hours. In Example 24 a further portion (50 microliters) of the sodium methoxide solution was added after 1 hour. The mixtures were then stored at ambient temperature for 48 hours and the solid which had been formed was collected by filtration and dried at 40° C. in vacuo to give dioxane-insoluble fractions of polymeric 3,3', 5,5'-tetraiodo-L-thyronine. The yields were Ex 24 0.014 g, Ex 25 0.220 g, Ex 26 0.260 g and Ex 27 0.290 g. The filtrates were added dropwise to hexane (15 ml) over 5 minutes. A precipitate formed which was allowed to settle. The supernatant was removed by decantation and the residue dried in vacuo at 40° C. to give dioxane-soluble fractions of polymeric 3,3', 5,5'-tetraiodo-L-thyronine as a yellow solid. Yield Ex 24 0.705 g, Ex 25 0.700 g, Ex 26 0.500 g and Ex 27 0.580 g.

EXAMPLE 28

A portion (10 microliters) of a solution of sodium methoxide (134 mg) in methanol (2 ml) was added to a solution of 3,3', 5,5'-tetraiodo-L-thyronine N-carboxy-anhydride (1 g prepared in Example 23) in dioxane (10 ml) and the mixture heated at 50° C. for 24 hours. The reaction mixture was centrifuged (3000 rpm for 5 minutes) and the supernatant removed by decantation. The residue was treated with dioxane (8 ml) and the resulting mixture centrifuged (3000 rpm for 5 minutes), and the residue was dried in vacuo at 38° C. to give polymeric 3,3', 5,5'-tetraiodo-L-thyronine. Yield 0.485 g.

EXAMPLE 29

A portion (10 microliters) of a 16% solution of N,N-diisopropylethylamine in dioxane was added to a solution of 3,3', 5,5'-tetraiodo-L-thyronine N-carboxy-anhydride (1 g prepared in Example 23) in dioxane (10 ml) and the mixture heated at 50° C. for 96 hours and then centrifuged (3000 rpm for 5 minutes). The supernatant was removed by decantation and the residue washed with dioxane (4 ml) and dried in vacuo at ambient temperature to give polymeric 3,3', 5,5'-tetra-iodo-L-thyronine. Yield 0.56 g.

EXAMPLE 30

A portion (5 microliters) of a 17.2% w/v solution of sodium methoxide in methanol was added to a solution of 3,3',5,5'-tetraiodo-L-thyronine N-carboxy-anhydride (1 g prepared in Example 23) in dioxane (10 ml) and the mixture heated at 50° C. for 20 hours. The volume of the reaction mixture was reduced to 3 to 4 ml and then the mixture was centrifuged (3000 rpm for 5 minutes) and the supernatant removed by decantation. The residue was washed with dioxane (1 ml) and water (2×2 ml) and then slurried with water (10 ml) and then cooled to −78° C. and dried in vacuo (0.1 mm Hg) to give polymeric 3,3',5,5'-tetraiodo-L-thyronine. Yield 0.550 g.

EXAMPLE 31

A portion (5 microliters) of a 17/2% w/v solution of sodium methoxide in methanol was added to a solution of 3,3',5,5'-tetraiodo-L-thyronine N-carboxyanhydride (1 g prepared in Example 23) in tetrahydrofuran (10 ml) and the mixture heated at 48° C. for 15 hours. Water was added to precipitate a solid which was separated by decantation. A portion of the wet solid (XX g) was cooled to −78° C. and dried in vacuo (0.1 mm Hg) to give polymeric 3,3',5,5'-tetraiodo-L-thyronine. Yield 0.300 g.

We claim:

1. A substantially pure synthetic iodothyronine polymer having 5 to 400 recurring units, which may be the same or different, of the formula I

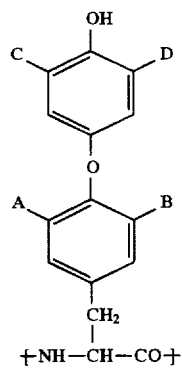

in which A is iodo and B, C and D are independently H or iodo with a hydrogen atom at the N-terminus and a hydroxy group at the C-terminus and N=5–400.

2. An iodothyronine polymer as claimed in claim 1 in which substantially all of the recurring units of formula I are L-stereoisomers.

3. An iodothyronine polymer as claimed in claim 1 in which A and C are iodo and B and D are independently H or iodo.

4. An iodothyronine polymer as claimed in claim 3 in which at least one of B and D is iodo.

5. An iodothyronine polymer as claimed in claim 1 in which the number of recurring units in the polymer is in the range 10 to 400.

6. The iodothyronine polymer of claim 1 in which A and C are both iodo and in which B and D are both iodo in 70 to 90% of the monomers and only one of B and D is iodo in the remaining 10 to 30% of the monomers.

7. An iodothyronine polymer as claimed in claim 6 in which R is the side chain from one or more amino acids selected from the group consisting of lysine, arginine, aspartic acid, glutamic acid, serine or threonine.

8. A pharmaceutical composition suitable for treating thyroid hormone deficiencies comprising a pharmaceutically acceptable diluent or carrier and a pharmaceutically effective amount sufficient to raise blood levels of thyroid hormones the polymer of claim 1. in which polymer substantially all of the recurring units of formula I are L-stereoisomers with a hydrogen atom at the N-terminus and hydroxy group at the C-terminus.

9. The pharmaceutical composition of claim 8 in in which A and C are both iodo and in which B and D are both iodo in 70 to 90% of the monomers and only one of B and D is iodo in the remaining 10 to 30% of the monomers.

10. A pharmaceutical composition as claimed in claim 8, in which at least one of B or D is iodo.

11. A pharmaceutical composition as claimed in claim 8, in which the pharmacologically active ingredient comprises a mixture of pharmaceutically effective amounts of a first iodothyronine polymer in which B, C and D are iodo and a second iodothyronine polymer in which B and C are iodo and D is H.

12. A pharmaceutical composition as claimed in claim 11, in which the molar ratio of the amount of the first iodothyronine polymer to the amount of the second iodothyronine polymer lies in the range 7:3 to 9:1.

13. A pharmaceutical composition as claimed in claim 11, which also comprises a pharmaceutically effective amount sufficient to raise blood levels of thyroid hormones, of a further iodothyronine polymer in which B is H and C and D are iodo.

14. A pharmaceutical composition as claimed in claim 13, in which the ratio of the amount of the first iodothyronine polymer to the amount of the second iodothyronine polymer to the amount of the further iodothyronine polymer is apporoximately 80:15:5.

15. A method of treating thyroid hormone deficiencies comprising administering to a patient a therapeutically effective amount of the synthetic iodothyronine polymer of claim 8 sufficient to raise levels of thyroid hormones.

16. The method of claim 15 in which A and C are both iodo and in which B and D are both iodo in 70 to 90% of the monomers and only one of B and D is iodo in the remaining 10 to 30% of the monomers.

17. A method of treating thyroid hormone deficiencies as claimed in claim 15 in which at least one of B or D is iodo.

18. An N-carboxyanhydride compound of formula III

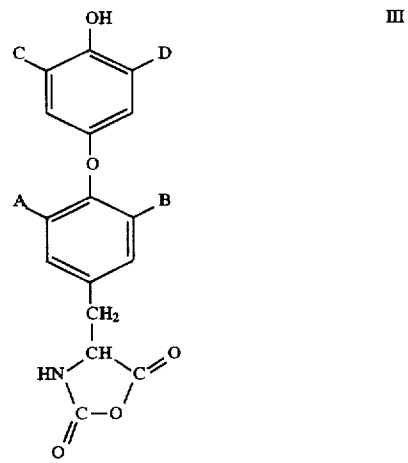

in which A is iodo and B, C and D are independently H or iodo provided that at least one of B, C or D is H.

19. The N-carboxyanhydride compound of claim 18 in which said N-carboxyanhydride is an L-stereoisomer and in which A and C are iodo and at least one of B and D is iodo.

20. An N-carboxyanhydride compound as claimed in claim 19, in which A and C are iodo and at least one of B and D is iodo.

* * * * *